(12) United States Patent
Ghadge et al.

(10) Patent No.: US 9,415,371 B2
(45) Date of Patent: Aug. 16, 2016

(54) MULTI-PHASE REACTOR SYSTEM WITH SLINGER LIQUID REFLUX DISTRIBUTOR

(71) Applicant: Reliance Industries Limited, Mumbai (IN)

(72) Inventors: Rajaram S. Ghadge, New Mumbai (IN); Thomas Mathew, New Mumbai (IN)

(73) Assignee: Reliance Industries Limited, Mumbai (IN)

( * ) Notice: Subject to any disclaimer, the term of this patent is extended or adjusted under 35 U.S.C. 154(b) by 0 days.

(21) Appl. No.: 14/394,228

(22) PCT Filed: Apr. 1, 2013

(86) PCT No.: PCT/IN2013/000214
§ 371 (c)(1),
(2) Date: Oct. 13, 2014

(87) PCT Pub. No.: WO2013/175489
PCT Pub. Date: Nov. 28, 2013

(65) Prior Publication Data
US 2015/0126771 A1    May 7, 2015

(30) Foreign Application Priority Data

Apr. 13, 2012   (IN) .......................... 1207/MUM/2012

(51) Int. Cl.
| | | |
|---|---|---|
| *C07C 51/265* | (2006.01) | |
| *B01J 19/18* | (2006.01) | |
| *B01F 5/22* | (2006.01) | |
| *B01J 10/00* | (2006.01) | |
| *B01J 19/00* | (2006.01) | |

(52) U.S. Cl.
CPC ............. *B01J 19/18* (2013.01); *B01F 5/221* (2013.01); *B01J 10/002* (2013.01); *B01J 19/0066* (2013.01); *C07C 51/265* (2013.01); *B01J 2219/0011* (2013.01); *B01J 2219/00101* (2013.01); *B01J 2219/00108* (2013.01); *B01J 2219/00252* (2013.01); *B01J 2219/194* (2013.01)

(58) Field of Classification Search
CPC .............................. C07C 51/265; C07C 63/26
See application file for complete search history.

(56) References Cited

U.S. PATENT DOCUMENTS

| | | |
|---|---|---|
| 1,759,629 A | 5/1930 | Riley |
| 2,917,241 A | 12/1959 | Waldrum |
| 4,422,626 A | 12/1983 | Baumgartner et al. |
| 4,898,331 A | 2/1990 | Hansen et al. |
| 5,226,605 A | 7/1993 | Bazergui et al. |
| 5,389,310 A | 2/1995 | Leiponen |
| 2011/0144384 A1* | 6/2011 | Piras et al. ................... 562/414 |

FOREIGN PATENT DOCUMENTS

| | | |
|---|---|---|
| CH | 229415 A | 10/1943 |
| FR | 2 570 959 A1 | 4/1986 |
| WO | 2008/036370 A2 | 3/2008 |
| WO | 2012/163511 A2 | 12/2012 |

OTHER PUBLICATIONS

International Search Report issued in PCT/IN2013/000214 mailed on Nov. 5, 2013 (3 pages).

* cited by examiner

*Primary Examiner* — Sudhakar Katakam
(74) *Attorney, Agent, or Firm* — Osha Liang LLP

(57) ABSTRACT

A multi-phase reactor system for performing multi-phase reactions is disclosed. The reactor system includes a reaction vessel having a slinger device (100) mounted on a centrally positioned agitator shaft (102) proximal to an operative top of the reaction vessel. The slinger device (100) comprises a holding means defined by a vertical circumferential plate (108) and a cover plate (107) for at least partially encasing the agitator shaft (102) to define a space for collecting a liquid. The holding means comprise at least one spraying means including spray pipes (106) for distributing the liquid on an inner wall of the reaction vessel by a projectile trajectory path on rotation of the agitator shaft. A concave blade (104) may be positioned over the cover plate (107) for preventing overflow of the liquid from the holding means and forming an umbrella of the flowing liquid to effect scrubbing of the vapors and off-gas.

2 Claims, 3 Drawing Sheets

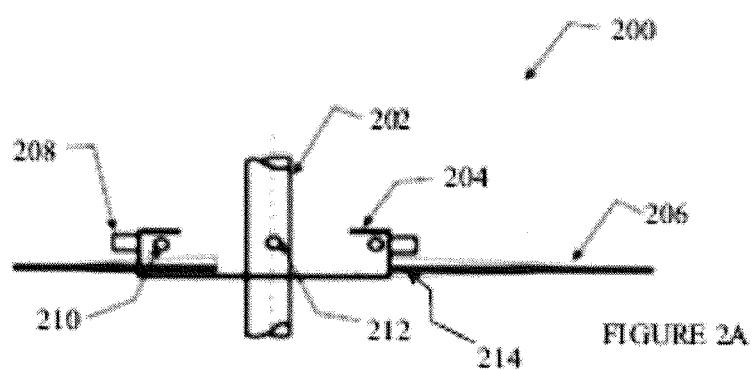
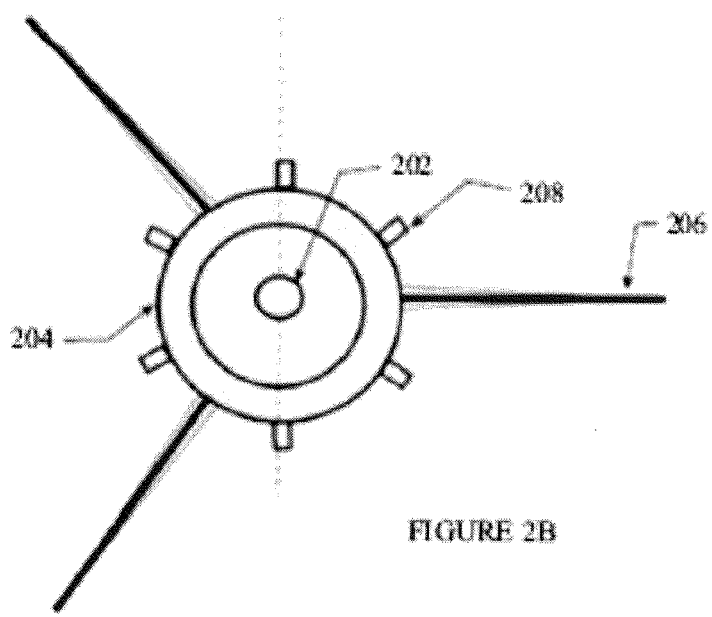

MULTI-PHASE REACTOR SYSTEM WITH SLINGER LIQUID REFLUX DISTRIBUTOR

FIELD OF DISCLOSURE

The present disclosure relates to multi-phase reactor systems for performing gas-liquid or gas-liquid-solid reactions and methods for conducting the reactions thereof.

BACKGROUND

A majority of the chemical reactions demand the configuration of the reactor system such as to provide high rate of production, selectivity towards the desired product, and negligible production of intermediate products and byproducts. Multi-phase reactor systems are specially designed for performing gas-liquid or gas-liquid-solid reactions. These reactor systems typically comprise a reaction vessel including baffles and agitation devices such as impellers, and are therefore commonly referred to as "stirred tank reactors" or "STR". Often, the reaction vessels also include gas spargers to disperse a gas into a bulk liquid medium. These multi-phase reactor systems are commonly used in fermentation, hydrogenation, phosgenation, neutralization, chlorination and oxidation reactions, where it is necessary to make intimate contact between the liquid and gas phase constituents to achieve the desired yield and production rate. Further, the reliable operation of these systems largely depends upon proper flow distribution and fluid dynamic behavior.

The configuration and geometry of the reaction vessel, impellers and gas spargers is mainly governed by the degree of homogeneity, required rate of mass transfer, solid suspension, and power consumption. Sometimes the nature of the chemical reaction demands auxiliary equipment or vessel internals like vessel jacket, internal heating or cooling coils and slinger devices.

Generally, in the gas-liquid or gas-liquid-solid reactions, gas is sparged at the bottom of the reaction vessel and feed is charged from the vessel top or middle. The unreacted gas leaves from the top liquid surface into an overhead system. This gas generally carries liquid droplets to the overhead system which causes fouling and corrosion in the overhead system. In exothermic reaction process, the heat of the reaction continuously boils the reactor liquid or the reaction medium which gets vaporized to maintain the required reaction temperature. These vapors also carry liquid droplets to the overhead system. In three-phase reactions, suspended solids from the reaction medium are also carried over by these vapors or unreacted gas to the overhead system causing solid built-up in the overhead system and solid deposition on the inner wall of the vessel headspace. Under these circumstances slinger devices are provided. In the known multi-phase reactor systems, a slinger device is provided near the operative top of the reaction vessel, typically on the agitator shaft of the reaction vessel, to spray a recycle liquid and/or fresh liquid over the free liquid surface of the reaction vessel and the vessel inner wall. The spraying of the liquid reduces both wall fouling and condenser plugging by washing the inner wall of the reaction vessel and scrubbing the gas leaving the reaction vessel.

An example of such multi-phase reaction is the oxidation of aromatic alkyls (e.g. p-xylene) within a liquid phase reaction medium, for e.g. the process of manufacturing terephthalic acid from p-xylene. In this process air is sparged through nozzles provided near the tip of the axial flow impellers in a reaction medium of solvent, catalyst, initiators and p-xylene. Heat generated by the exothermic oxidation reaction is dissipated by the vaporization of the solvent and the water produced by the oxidation of p-xylene. The temperature in the reaction vessel is controlled by the vaporization of the solvent and water and by recycle of the condensate stream of the overhead vapors. Crude terephthalic acid is recovered from the reaction product by crystallization and filtration.

Most of the terephthalic acid crystals is suspended within the liquid phase and can build-up on the walls of the reaction vessel. This causes reduction in the operating volume of the reactor, decreases the residence time of the reaction, and results in the formation of intermediate byproduct. Vaporization of the solvent from the reaction vessel can also carry fine solid particles to the overhead condenser system which leads to plugging of the overhead condenser tubes. The uneven heating and cooling of the reaction vessel wall also causes a thermal stresses at the vessel shell and can lead to shell leak. In such continuous boiling oxidation reaction vessel of a terephthalic acid manufacturing plant, condensate stream of the overhead vapors is fed back to the reaction vessel through a top and bottom reflux line. The objective of top reflux is to wash the reaction vessel wall to avoid any solid deposition and scrub the vapors containing solid particles entering into the overhead condenser system. The objective of the bottom reflux is to increase the conversion of p-xylene to terephthalic acid and reduce the acetic acid burning by reducing the severity of reaction vessel.

However, the conventional slinger devices consist of rotating, flat circular disks comprising multiple vertically raised straight vanes extending radially outward from a center hub of the disc to its outer periphery. The condensate is returned to the reaction vessel via a conduit located above the slinger device. The condensate is fed onto the slinger device from where it is subsequently distributed radially outward about the reaction vessel. These slinger devices, which are located in the upper "head space" section of the vessel, cover only a portion of the reaction vessel cross-section, and are therefore incapable of completely eliminating the above-mentioned problems. Some of such traditional slinger devices are disclosed in the prior art below.

U.S. Pat. No. 4,422,626 discloses an apparatus for building-up and repairing a refractory lining of an industrial furnace. The apparatus consisting of a rotary disc centrifugally throwing particulate refractory material against a portion of the lining to be repaired and comprising a horizontal row of hollow bolts with bores to spray water into an inlet conduit of annular cross section whereby the material passing through the conduit to the disc will be uniformly wetted.

WO2008036370 discloses a liquid-gas phase reactor system comprising a slinger secured to a drive shaft extending through at least a portion of an upper section of a reaction vessel and located below a first liquid inlet, wherein the slinger comprises an upper horizontal surface including a plurality of vertically raised vanes extending radially outward along a curved path.

A major shortcoming of the known slinger devices is that a large portion of the condensate is distributed only over a limited cross-section of the reaction vessel very little condensate actually reaching the reactor walls. Another shortcoming is that liquid tends to be distributed in large droplets rather than finely divided droplets. This results in solid carryover in the overhead condenser system and also solid deposition on the reactor wall. Consequently, such systems experience wall fouling, condenser plugging, and poor mixing of condensate with the liquid, phase reaction medium. Moreover, the known slinger devices are less effective at dissipating heat generated by the exothermic reactions. For example, with the exothermic oxidation of aromatic alkyls, much of the heat generated by the reaction is concentrated in the middle section of the liquid reaction medium. The hot spots can lead to undesired reactions, consumption of solvent and increased vapor generation; all of which contribute to higher operating costs and lower efficiency. Further, the uneven heating and cooling of the reaction vessel wall can produce thermal stresses at the vessel wall which can cause the shell leakage.

There is therefore felt a need to provide an improved slinger device for use in a multi-phase reactor system, which will overcome the afore-mentioned shortcomings of the known slinger devices by spreading the reflux (condensate) liquid uniformly about the inner walls of reaction vessel and optimizing the top reflux quantity as per the process requirements.

OBJECTS

Some of the objects of the present disclosure, which at least one embodiment herein satisfies, are as follows:

It is an object of the present disclosure to ameliorate one or more problems of the prior art or to at least provide a useful alternative.

Accordingly, an object of the present disclosure is to provide an improved slinger device for a multi-phase reactor system which minimizes solid build-up in the overhead system and solid deposition on the inner shell wall of the reaction vessel headspace by cleaning the inner shell wall of solid deposits and scrubbing the solid particles from outgoing vapors and off-gas, thereby reducing both inner shell fouling and overhead system plugging to enhance the reactor operational life.

Another object of the present disclosure is to provide a slinger device for a multi-phase reactor system which spreads the liquid and/or the liquid reflux uniformly at 360° on the inner shell wall of the reaction vessel in the vapor space.

Yet another object of the present disclosure is to provide a slinger device for a multi-phase reactor system which optimizes the top reflux quantity as per the process requirements.

Other objects and advantages of the present disclosure will be more apparent from the following description when read in conjunction with the accompanying figures, which are not intended to limit the scope of the present disclosure.

SUMMARY

In accordance with the present disclosure, there is provided a multi-phase reactor system for performing multi-phase reactions, the reactor system including a reaction vessel having a slinger device mounted on a centrally positioned agitator shaft proximal to an operative top of the reaction vessel, wherein the slinger device comprises a holding means defined by a vertical circumferential plate and a cover plate at least partially encasing the agitator shaft to define a space for collecting a liquid, the holding means being provided with at least one spraying means for distributing the liquid on an inner wall of the reaction vessel by a projectile trajectory path on rotation of the agitator shaft.

Typically, in accordance with the present disclosure, the holding means is provided in operative communication with a liquid inlet to receive the liquid.

Typically, the slinger device rotates synchronously with the agitator shaft.

Preferably, in accordance with the present disclosure, the spraying means comprise at least one spray pipe provided on the vertical circumferential plate.

Typically, in accordance with the present disclosure, the spraying means comprise a plurality of equally spaced circumferential tubes provided on the vertical circumferential plate, the circumferential tubes being adapted for forming an umbrella of the liquid for scrubbing the vapors generated during the reaction off solids before exiting the reaction system.

Preferably, in accordance with the present disclosure, the circumferential tubes have a smaller length than the spray pipe.

Alternatively, in accordance with the present disclosure, the spraying means comprise at least one concave blade provided on the cover plate, the concave blade being adapted for preventing overflow of the liquid and forming an umbrella of the liquid for scrubbing the vapors generated during the reaction off solids before exiting the reaction system.

Typically, in accordance with the present disclosure, the diameter of the slinger device is adapted to provide a vapor exit velocity from the reactor system in the range of 1 to 5 m/s.

In accordance with the present disclosure, there is disclosed a method for oxidizing an aromatic alkyl in a multi-phase reactor system, the method comprises the following steps:

introducing a liquid reaction medium comprising the aromatic alkyl and a solvent in a reaction vessel of the reactor system;

sparging air into the liquid reaction medium at a location proximal to an operative bottom of the reaction vessel to effect the oxidation which generates heat and causes vaporization of the liquid reaction medium;

condensing at least a portion of the vapors of the liquid reaction medium to generate a reflux liquid;

returning a first portion of the reflux liquid to the reaction vessel through a slinger device mounted on a centrally positioned agitator shaft proximal to an operative top of the reaction vessel for cleaning the inner wall of the reaction vessel off solid deposits and scrubbing solid particles from outgoing vapors and off-gas, wherein the slinger device comprises a holding means defined by a vertical circumferential plate and a cover plate at least partially encasing the agitator shaft to define a space for collecting the reflux liquid, the holding means being provided with at least one spraying means for distributing the reflux liquid on the inner wall by a projectile trajectory path on rotation of the agitator shaft; and returning a second portion of the reflux liquid into the liquid reaction medium.

BRIEF DESCRIPTION OF THE ACCOMPANYING DRAWINGS

The present disclosure will now be described with the help of the non-limiting accompanying drawings, in which, FIG. 1A illustrates the schematic of a side-view of a first embodiment of the slinger device for a multi-phase reactor system;

FIG. 2A illustrates the schematic of a side-view of a second embodiment of the slinger device for a multi-phase reactor system;

FIG. 2B illustrates the schematic of a top-view of the second embodiment of the slinger device for a multi-phase reactor system.

DETAILED DESCRIPTION

Figure 1A:
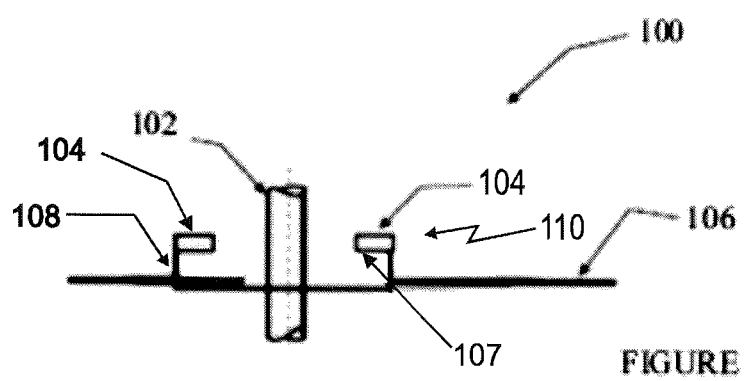
FIG. 1B illustrates the schematic of a top-view of the first embodiment of the slinger device for a multi-phase reactor system.

The disclosure will now be described with reference to the embodiments which do not limit the scope and ambit of the disclosure. The description provided is purely by way of example and illustration.

The embodiments herein and the various features and advantageous details thereof are explained with reference to the non-limiting embodiments in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The present disclosure envisages a multi-phase reactor system for performing multi-phase reactions, including gas-liquid or gas-liquid-solid reactions, preferably oxidation reactions of aromatic alkyls. The multi-phase reactor system comprises a reaction vessel, single or multiple impellers, gas or air spargers, a feed inlet and/or liquid inlet and a slinger device mounted on an agitator shaft. The slinger device installed on the agitator shaft is used to spread a liquid and/or a reflux liquid uniformly at 360° on the inner shell wall of the reaction vessel in the vapor space thereof, to keep the inner shell wall of the reaction vessel clean, and also scrub the solid particles carried in the off-gas and vapors conveyed from the reaction vessel.

The slinger device of the present disclosure ensures complete wetting and cleaning of the inner wall, headspace of the reaction vessel and scrubbing of the reaction vapors. The slinger device is mounted on the agitator shaft which is centrally positioned extending from operative top of the reaction vessel through at least a portion of operative length of the reaction vessel. The slinger device is positioned proximal to the operative top of the reaction vessel. The slinger device comprises a holding means which is formed by a vertical circumferential plate and a cover plate at least partially encasing the agitator shaft to define a space adapted to collect a liquid. The holding means is provided with at least one spraying means which are adapted to distribute the liquid from the holding means on, the inner wall of the reaction vessel by a projectile trajectory path on rotation of the agitator shaft. The spraying means typically comprise at least one spray pipe mounted on the vertical circumferential plate. The spraying means may comprise a plurality of equally spaced circumferential tubes arranged on the vertical circumferential plate and having a length smaller than the spray pipe. The circumferential tubes may or may not be arranged in the same line as the spray pipe. The circumferential tubes are adapted to form an umbrella of the liquid for scrubbing the vapors generated during the reaction of solids such that only clean vapors and off-gas exit the reaction vessel. Alternatively, the spraying means may comprise at least one concave blade mounted on the cover plate. The concave blade prevents the liquid from the holding means from overflowing and is also adapted to form an umbrella of the liquid for scrubbing the vapors generated during the reaction of solids.

A portion of the agitator shaft is surrounded by the vertical circumferential plate and a doughnut-shaped cover plate is placed along the edge of the circumferential plate to define an annular space, between the agitator shaft and the circumferential plate, adapted to receive the liquid. The spraying means typically comprise at least one spray pipe mounted on the vertical circumferential plate. More than one equally spaced spray pipes having appropriate diameter and designed to provide sufficient clearance between the inner wall of the reaction vessel and the discharge point of the pipes may be provided. These pipes are mounted on the circumferential plate of the slinger device to spray the liquid collected in the annular space on the inner wall of the reaction vessel. The spraying means may further comprise one or more equally spaced concave blades positioned on the cover plate of the slinger device. The concave blades have appropriate blade height and length equal to width of the cover plate. The spraying means may also comprise plurality of equally spaced circumferential tubes provided on the circumferential plate.

The multi-phase reactor system is suitable for oxidizing aromatic alkyls, e.g. p-xylene. A liquid reaction medium comprising the aromatic alkyl and a solvent, typically acetic acid, is charged in the reaction vessel of the multi-phase reactor. Air is sparged in the liquid reaction medium by means of gas spargers provided below the liquid level to provide a source of oxygen to initiate the oxidation reaction. The heat generated by the exothermic oxidation reaction is dissipated by the vaporization of the solvent and water produced by the oxidation of the aromatic alkyl. The vaporized solvent is condensed in an overhead condenser and less than 50% of the total condensate (reflux liquid) is recycled to the liquid reaction medium by means of the slinger device located at the operative top of the reactor vessel and more than 50% of the total condensate is returned to the reactor vessel through a bottom reflux line. The reactor system comprises a top reflux line which, delivers the reflux liquid to the holding means via a liquid inlet of the slinger device.

Recycled liquid falling in the holding means is distributed over the liquid surface as well as over the inner wall of the reaction vessel. It is necessary to quantify the exact amount of liquid flow over the holding means and the flow through the rotating spray pipes and circumferential tubes to estimate the liquid velocity passing through it. The liquid spray over the inner wall of the reaction vessel corresponds to the quantity of liquid that passes through the spray pipes. Remaining liquid is distributed over the liquid medium in the reaction vessel.

In stirred tank reactors speed of agitation is governed by the required power consumption per unit volume and mass transfer for the desired rate of reaction. As the slinger is mounted on the agitator shaft, it rotates with the given speed of the agitator. Therefore, the stinger device is required to be designed for the known speed of the agitator. The vapor or the unreacted gas leaving the free liquid surface of the reaction vessel flows through the region between the vessel wall and the slinger device. The velocity of this gas or vapor decides the diameter of the stinger device. The stinger device diameter is calculated such as to maintain the vapor exit velocity from the reaction vessel in an appropriate range typically 1-5 m/s.

The embodiments of the present disclosure are illustrated in the FIG. 1 and the FIG. 2 of the accompanying drawings.

FIG. 1A of the accompanying drawings illustrates a side-view of a first embodiment of the slinger device of the present disclosure. The slinger device 100 typically in the form of a bucket comprises a vertical circumferential plate 108 and a cover plate 107 encasing a portion of an agitator shaft 102 to define holding means. An arrangement 110 includes a plurality of concave blades 104 (not specifically shown in the FIG. 1A) placed over the cover plate 107. The slinger device 100 rotates synchronously with the agitator shaft 102. The slinger device 100 comprises spraying means including a plurality of spray pipes 106. The reflux liquid is received in the holding means. The reflux liquid flows through the rotating spray pipes 106 and is distributed over the entire cross section area of the reaction vessel inner wall. The concave blades 104 prevent overflowing of the holding means. Further, the concave blades 104 are adapted to form an umbrella of the flowing reflux liquid which scrubs the vapor and off-gas generated during the reaction of solids and thereby provides clean vapor and off-gas at the exit.

Figure 1B:
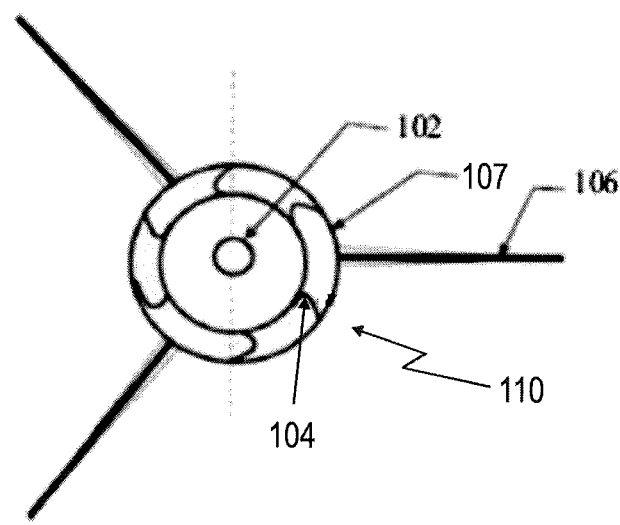

FIG. 1B of the accompanying drawing illustrates a top-view of the first embodiment of the slinger device of the present disclosure. FIG. 1B shows an arrangement 110 that includes a plurality of concave blades 104 placed over the cover plate 107. An open space is defined between the agitator shaft 102 and the arrangement 110 which allows the reflux liquid to flow in the form of an umbrella, this helps in scrubbing the vapors and off-gas generated during the reaction. The spray pipes 106 spread the reflux liquid at 360° C. on the inner wall of the reaction vessel.

FIG. 2A of the accompanying drawings illustrates a side-view of a second embodiment of the stinger device of the present disclosure. The slinger device 200 comprises a vertical circumferential plate 214 and a cover plate 204 which encase a portion of an agitator shaft 202 to define holding means. The slinger device 200 comprises spraying means including a plurality of spray pipes 206 and a plurality of circumferential tubes 208, 210 & 212. The plurality of circumferential tubes 208, 210 & 212 have equal diameter and length and are equi-spaced on the circumferential plate 214 of the slinger device 200. The length of the circumferential tubes 208, 210 & 212 is smaller than the length of the spray pipes 206. The plurality of the circumferential tubes 208, 210 & 212 may or may not be placed in-line with the spray pipes 206. The reflux liquid is received in the holding means. The reflux liquid flows through the rotating spray pipes 206 and the plurality of circumferential tubes 208, 210 & 212 and is distributed over the entire cross section area of the reaction vessel inner wall. The plurality of circumferential tubes 208, 210 & 212 are adapted to form an umbrella of the reflux liquid for scrubbing the vapors generated during the reaction of solids to provide clean vapors and off-gas at the exit of the reaction vessel.

FIG. 2B of the accompanying drawings illustrates a top-view of the second embodiment of the slinger device of the present disclosure. FIG. 2B shows the holding means defined between the agitator shaft 202 and the cover plate 204. The arrangement of the spray pipes 206 and the plurality of circumferential tubes 208, 210 & 212 on the circumferential plate 214 is clearly shown from the top-view.

The kinetic energy of the fluid at the exit of the spray pipe/tubes is the addition of energy created by the static head developed by the liquid from the holding means and energy due to the centrifugal force acting on the liquid. A centrifugal-force driven fluid flow in the rotating pipe/tubes is subjected to coriolis forces in addition to the pressure gradient in the circular pipe. The liquid velocity at the exit of the rotating pipe/tubes or rotating vessel is estimated by subtracting frictional losses in the rotating pipe/tubes and orifice from the total of static head and centrifugal force. When liquid is thrown out of the pipe or tubes with an initial liquid velocity it follows the projectile trajectory path. The liquid velocity at the exit of spray pipe/tubes decides the distribution pattern of liquid flowing over the open space of the reaction vessel cross section and the height at which majority of the liquid droplets are hitting the reactor inner wall. The liquid thrown with initial liquid velocity first travels into the vertical plane and then it moves into two-dimensions under the action of gravity and the friction offered by the upward vapor or gas. The time required for the liquid droplet to travel the distance between the slinger device and the vessel wall is estimated using the equation of motion by considering zero acceleration along the horizontal axis. The vertical distance at which the liquid droplet hit the wall is estimated using the equation of motion for the known travel time under the influence of friction offered by vapor rise velocity and gravity. The velocity of the liquid leaving the spray pipe/tubes or slinger device is optimized by varying the number of pipes, the pipe diameter, the number of circumferential tubes, the size of the circumferential tubes and the number of concave blades, thereby identifying the required location at which the liquid droplet should hit the vessel wall.

Figure 3:
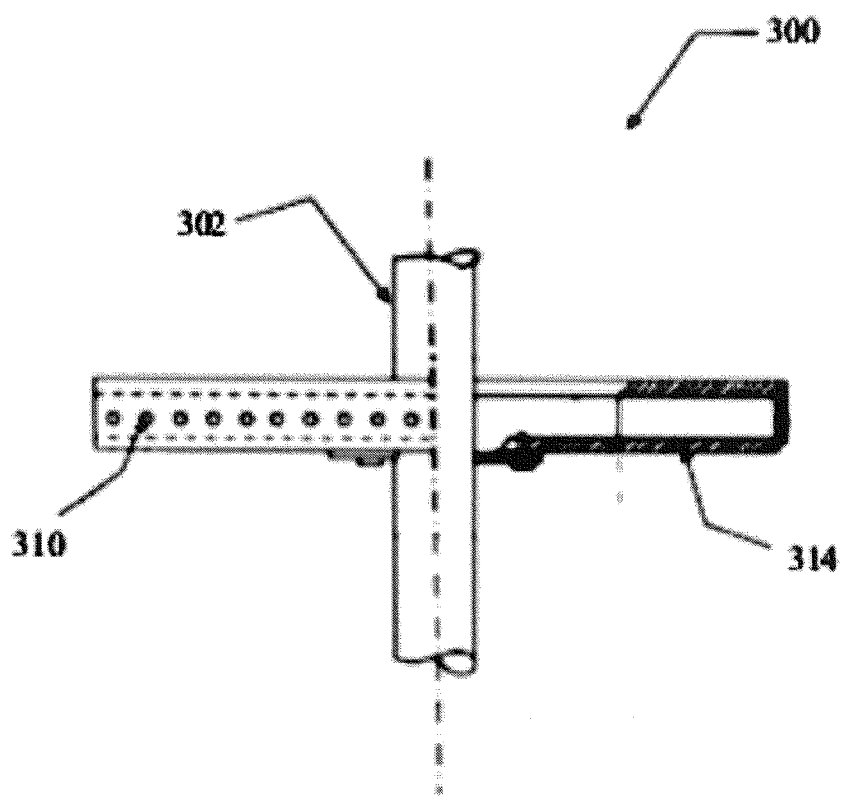
FIG. 3 illustrates the schematic of the slinger plate design.

An embodiment of the circumferential plate design is illustrated in the FIG. 3 of the accompanying drawings. The slinger device 300 shows a circumferential plate 314 surrounding an agitator shaft 302 and having a plurality of equally spaced circumferential or spiral tubes 310 typically at a distance of 10 mm each. The circumferential velocity is estimated by orifice meter calculation and the place at which the liquid falls on the inner wall is estimated using a projectile equation. The velocity of the reflux liquid at the circumference of circumferential plate 314 is based on the centrifugal force exerted by the speed of agitation and the slinger diameter on the circumferential plate area. The % free area on the circumferential plate 314 varies with the number of tubes and their diameter. This is optimized in such a way that the reflux liquid will fall on the inner wall of the reaction vessel. Trajectories of the liquid jet will be uplifted by the vapor/gas flowing upward. Hence the liquid jet will meet the wall at higher elevation than calculated.

TECHNICAL ADVANTAGES

A slinger device for a multi-phase reactor system, as described in the present disclosure has several technical advantages including but not limited to the realization of: the slinger device provides a uniform spread of the reflux liquid at 360° along the inner shell wall of the reaction vessel; the slinger device scrubs solid particles in the off-gas and vapors conveyed from the reaction vessel; and the slinger device optimizes the top reflux quantity as per the process requirements, whereby the surplus reflux can be diverted to the reaction vessel bottom to provide cold bottom reflux.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

Any discussion of documents, acts, materials, devices, articles or the like that has been included in this specification is solely for the purpose of providing a context for the disclosure. It is not to be taken as an admission that any or all of these matters form part of the prior art base or were common general knowledge in the field relevant to the disclosure as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of embodiments, those skilled in the art will recognize that the embodiments herein can be practiced with modification within the spirit and scope of the embodiments as described herein.

The invention claimed is:

1. A method for oxidizing an aromatic alkyl in a multi-phase reactor system, said method comprising the following steps:

introducing a liquid reaction medium comprising the aromatic alkyl and a solvent in a reaction vessel of said reactor system;

sparging air into said liquid reaction medium at a location proximal to an operative bottom of said reaction vessel to effect the oxidation which generates heat and causes vaporization of said liquid reaction medium;

condensing at least a portion of said vapors of said liquid reaction medium to generate a reflux liquid;

returning a first portion of said reflux liquid to said reaction vessel through a slinger device mounted on a centrally positioned agitator shaft proximal to an operative top of said reaction vessel for cleaning the inner wall of said reaction vessel of solid deposits and scrubbing solid particles from outgoing vapors and off-gas, wherein said slinger device comprises a holding means defined by a vertical circumferential plate and a cover plate at least partially encasing said agitator shaft to define a space for collecting said reflux liquid, said holding means being provided with a plurality of types of spraying means for uniformly distributing said reflux liquid on said inner wall by a projectile trajectory path on rotation of said agitator shaft, wherein the projectile trajectory path distributes said reflux liquid 360° on said inner wall and the plurality of types of spraying means comprises at least one spray pipe provided on the vertical circumferential plate and a plurality of equally spaced circumferential tubes provided on the vertical circumferential plate; and returning a second portion of said reflux liquid into said liquid reaction medium.

2. The method of claim 1, wherein the slinger device further comprises concave blades on the cover plate, wherein said plurality of equally spaced circumferential tubes and said concave blades are adapted to form an umbrella of said reflux liquid for scrubbing said outgoing vapors.

* * * * *